United States Patent [19]

Martinelli et al.

[11] 4,295,829
[45] Oct. 20, 1981

[54] TOOL HOLDER

[76] Inventors: Claude Martinelli; Marcelle Martinelli epouse Boisson, both of 5, Place du Marche, Gracay, France, 18310

[21] Appl. No.: 58,379

[22] Filed: Jul. 17, 1979

[30] Foreign Application Priority Data

Aug. 8, 1978 [FR] France ................ 78 23369

[51] Int. Cl.³ .................... A61C 1/02; B25G 3/00
[52] U.S. Cl. ........................ 433/99; 433/130; 433/133; 403/33; 173/163
[58] Field of Search .............. 403/33; 433/130, 133, 433/127, 99; 173/163, 50

[56] References Cited

U.S. PATENT DOCUMENTS

| | | | |
|---|---|---|---|
| 628,524 | 7/1899 | Case et al. ............ | 433/130 |
| 1,678,096 | 7/1928 | Andresen ............ | 433/130 |
| 1,984,663 | 2/1934 | Tatham ............ | 433/130 X |
| 2,025,779 | 12/1935 | Roelke ............ | 433/130 X |
| 3,120,845 | 2/1964 | Horner ............ | 173/163 UX |
| 3,727,312 | 4/1973 | Durante ............ | 433/130 |
| 3,756,090 | 9/1973 | Mella et al. ............ | 173/163 X |
| 4,004,344 | 1/1977 | Gold et al. ............ | 433/133 |

FOREIGN PATENT DOCUMENTS

| | | |
|---|---|---|
| 876136 | 7/1954 | Fed. Rep. of Germany . |
| 599738 | 10/1925 | France . |
| 679898 | 1/1930 | France . |
| 799430 | 4/1936 | France . |
| 922557 | 2/1947 | France . |
| 1248093 | 10/1960 | France . |
| Ad.75885 | 7/1961 | France . |
| 1578769 | 7/1969 | France . |
| 1583476 | 10/1969 | France . |
| 233038 | 6/1944 | Switzerland . |

*Primary Examiner*—James Kee Chi
*Attorney, Agent, or Firm*—Sandler & Greenblum

[57] ABSTRACT

A tool holder having a bent handle and having first and second ends. The holder comprises a head comprising means for receiving the tool. The head is arranged at the first end of the tool holder. The holder further comprises an operating knob arranged intermediate the first and second ends of the holder and securing means for securing the head to the holder. An auxiliary operating knob is arranged at the second end of the holder on the handle. A multiplier system provides for the desired magnitude of movement of the tool in response to movement of the operating knob.

18 Claims, 5 Drawing Figures

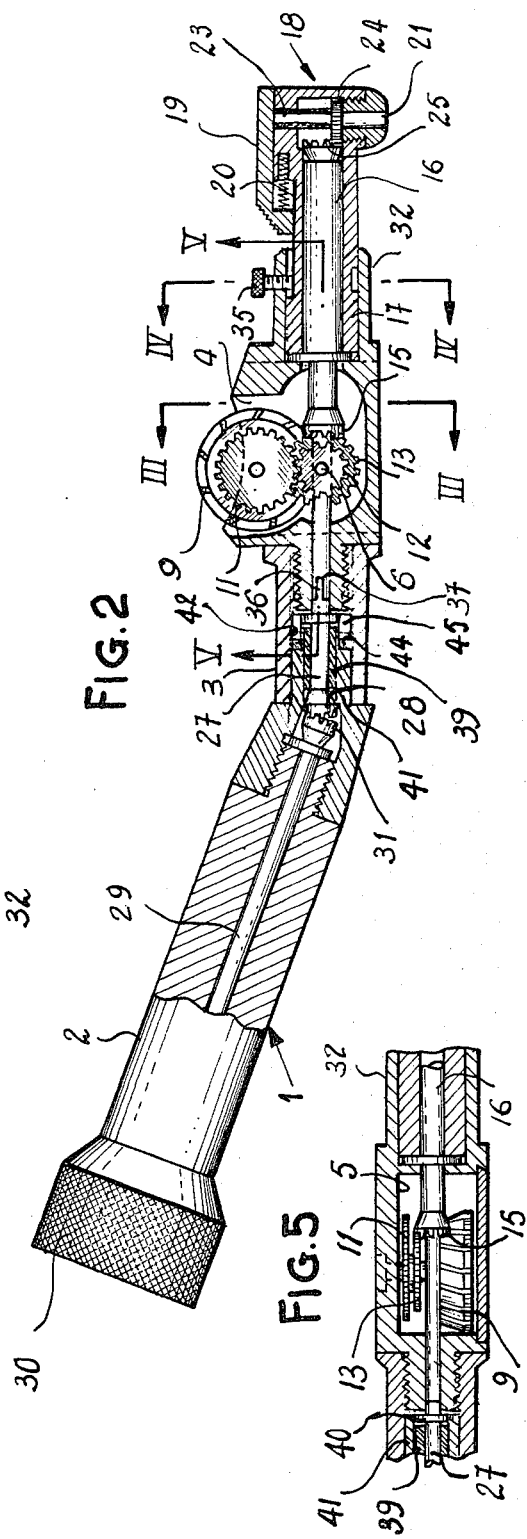

TOOL HOLDER

BACKGROUND OF THE INVENTION

1. Field of the Invention

The present invention relates to a tool holding device which finds particular application in dentistry and which may be specifically designed to support very small tools such as nerve extractors, drill pins, dental cement insertion tools, screwdrivers, and the like.

2. Description of the Prior Art

The use of nerve extractors is a very delicate operation by virtue of the small size of the instrument and also because the dentist is required to hold the extractor between his thumb and index finger which obstructs the patient's mouth such that the dentist cannot see clearly.

By virtue of the fact that the instruments used slip from the dentist's fingers, there is a risk that the patient will swallow the instruments. Therefore, instruments of the kind used have been connected to small chains integral with a ring placed on the dentist's finger. While such a device serves to eliminate the risk of the patient swallowing the device, the arrangement necessarily impedes the dentist's work.

A tool holder has been suggested which comprises a rectilinear handle having one end fitted with an operating knob which drives a shaft journalled in the handle. The free end of the shaft has a pinion which interacts with a pinion of a head adapted to accommodate the tool such that the tool extends perpendicularly to the handle. A device of this type is described, in detail, in French Pat. No. 679,898, Aug. 5, 1929, and suffers from several drawbacks. In a device disclosed in the patent, the practitioner holds the handle by gripping a portion near the tool head between his index finger and his thumb. The handle rests, at one end, on the edge of the middle finger, and at the other end on the outer part of the hand extending between the index finger and the thumb. The knob must, therefore, be operated with the other hand, such that work performed with the tool holder is inaccurate because operation of the knob with the other hand causes the tool holder to move.

German Pat. No. 876,136, July 8, 1949, to a certain extent overcomes the drawback of the previously discussed device, by substituting a side knob situated in an intermediate portion along the handle for the operating knob. Such an arrangement enables the tool head to be manipulated by the index finger of the hand in which the tool is held thus resulting in far greater precision.

The device of the German patent comprises a handle having two parts which may form an angle between them. One of the parts comprises the operating knob along its side and is rotatable along its longitudinal axis with relation to the other part of the handle. Such an arrangement normally permits the user's hand to exercise full control over the tool holder whatever the direction in which the tool is being operated. Nevertheless, in reality, a device of this type is not practical since in order to operate on the upper teeth, the user must an uncomfortable position.

French Pat. No. 1,583,476 describes a manual instrument comprising a rectilinear handle provided at one of its ends with an adjustable head linked by a kinematic connection to an operating knob situated at the other end of the handle. The kinematic connection comprises a milled nut extending through an aperture provided in the handle at a point along its length such that the portion of the tool head which receives the tool itself can be rotated either at the end of the handle or by means of the intermediate nut.

Such a device is not practical in that it cannot be firmly held by the user. In operation, the holder must be held with the various fingers of the hand against the palm while the thumb is used to operate the intermediate nut.

When used, it has been found that the movements exerted by the thumb for rotating the nut cause the hand itself to move such that the operation being performed lacks precision.

SUMMARY OF THE INVENTION

It is, therefore, an object of the invention to provide a tool holder which conveniently provides access to the various areas of the mouth while nevertheless providing a clear field of view.

It is a further object of the invention to provide a tool holder which may be used in a manner which does not interfere with the steadiness of the user's hand while nevertheless effectively performing its function.

These and other objects are fulfilled by means of the tool holder of the invention which has a bent handle and has first and second ends. The tool holder comprises a head having means for receiving a tool; the head being arranged at the first end of the tool holder. An operating knob is arranged intermediate the first and second ends of the tool holder and is operatively associated with the head whereby rotation of the operating knob results in movement of the head. Securing means are provided for securing the head to the holder in a fixed angular position relative to the holder; the angular position of the head being adjustable relative to the handle. An auxiliary operating knob is arranged at the second end of the holder on the handle and is operatively associated with the head whereby rotation of the auxiliary operating knob results in movement of the tool which is eventually inserted in the head. Finally, a multiplier system provides the desired magnitude of movement of the tool in response to movement of the operating knob.

In a preferred embodiment of the invention the holder is provided with a decoupling means whereby the auxiliary operating knob is deactivated relative to the head.

BRIEF DESCRIPTION OF DRAWINGS

With reference to the annexed drawings;

FIG. 1 is a perspective view of the device of the invention;

FIG. 2 illustrates the axial cross-section of the device shown in FIG. 1;

FIG. 3 is a cross-sectional view along the line III—III of FIG. 2;

FIG. 4 is a cross-sectional view along the line IV—IV of FIG. 2; and

FIG. 5 is a cross-sectional view along the line V—V of FIG. 2.

DESCRIPTION OF PREFERRED EMBODIMENTS

The tool holder of the invention is of the type having a bent handle of which one end is fitted with a head comprising means for receiving and affixing a tool. The head is designed such that when inserted properly, the tool extends perpendicularly to the portion of the handle adjacent to the tool head. The tool head is kinematically or operatively connected to an operating knob situated along an intermediate point on the handle. An auxiliary operating knob is situated on the second end of the handle. The tool head is mounted such that it may rotate along the longitudinal axis on the corresponding end of the handle. Means are provided for securing the end of the device comprising the tool head at the desired angle. The operating knob situated at a point intermediate along the handle of the tool head is itself kinematically or operatively connected to the head via a multiplier system. The bend in the handle is situated approximately midway along its length and forms an angle of between about 130 to 160 degrees. The operating knob is positioned in the vicinity of the head and inside the angle formed.

By virtue of the structure of the tool holder of the invention, the holder may be firmly held between the middle finger and the thumb and allowed to rest in the fleshy part of the hand extending from the index finger to the thumb. The index finger itself is free to operate the knob. By virtue of the multiplier connected to the operating knob, the tool head is rotated to a considerable extent with even very limited amplitudes of movement of the knob, thus increasing the operating accuracy because the tool is rotated through a wide angle without the necessity of substantial movement of the index finger which might normally cause the holder to move unsteadily.

In a preferred embodiment of the invention, the holder is provided with decoupling means for disconnecting the auxiliary operating knob situated at the free end of the handle. By decoupling the auxiliary operating knob when not in use, friction is reduced and rotation of the operating knob may be performed even more gently and with less effort.

In one embodiment of the invention, the handle comprises two sections joined together by a bayonet system. The head is kinematically or operatively associated with the auxiliary operating knob by means of a linkage which comprises a shaft having a stub or other means for operatively associating the shaft with the rest of the linkage. The shaft itself is removably or retractably mounted within the holder. Thus, the shaft stub or other means may be withdrawn thereby deactivating the auxiliary operating knob.

The operating knob is frustroconically shaped and is arranged such that the small base of the knob is arranged in a plane which passes through the median longitudinal axis of the handle. Therefore, additional space is provided to permit passage of the linkage which drives the head, thus resulting in a particularly compact device which provides the dentist with a maximum field of operation.

Finally, according to yet another preferred embodiment of the invention, the operating knob is integral with a first pinion having a large diameter which drives a second pinion having a small diameter which is co-axially mounted on a small shaft with a third pinion of large diameter which meshes and interacts with a cylindrically arranged system of teeth having a small diameter which is arranged on a head shaft connected to the means for driving the tool head.

With reference to the drawings, the device shown comprises a handle 1, comprising first and second elements 2 and 3. The first and second elements are bent so as to form an angle between them.

Element 3 comprises a housing 4 having a wall 5 open at its top. Two small shafts or pins 6 and 7 are journalled therein. The pin 7 is keyed to operating knob 9 having the general shape of a truncated cone, having lateral corrugations. A first pinion 11 is also keyed onto the pin 7. First pinion 11 engages a second pinion 12 keyed onto pin 6. A third pinion 13, of greater diameter than the second pinion, is also keyed onto pin 6. The third pinion interacts with a system of teeth 15 arranged at one of the ends of a shaft 16 which is journalled in a sleeve 17 whose free end bears head 18.

Head 18 is of the type normally used in dentistry and comprises a pusher 19 which moves in opposition to a spring 20 and which is able to key the shank of a tool engaged in conduit 21 of the head. The conduit 21 is arranged to extend perpendicularly to the axis of second element 3.

A sleeve 23 adapted to receive the tool is journalled into the head 18 and comprises a fourth pinion 24 which interacts with a second system of teeth 25 on the corresponding end of the shaft 16.

At its free end, the shaft 16 comprises a slot 37 adapted to receive a flattened portion 36 of the shaft 27. The shaft 27 comprises a system of teeth 28 at its other end which interacts with a system of teeth 31 of shaft 29 journalled into element 2 and integral with auxiliary operating knob 30.

Shaft 27 is fitted within a sleeve 39 and comprises a ferrule 40. Element 2 has a bent extension or prolongation 41 which itself acts as an outer sleeve to accommodate sleeve 39. The prolongation or extension 41 is received within a bore 42 of element 3. Bore 42 is provided with lugs 44 which interact with angled slots 45 in extension 41 so as to form a bayonet-type assembly.

Although one particular bayonet assembly has been illustrated, the invention is not limited to the particular assembly shown and other types of bayonet assemblies may quite obviously be used.

Sleeve 17 engages a socket 32 provided in element 3 and is free to rotate within the socket. Sleeve 17 comprises a groove 33 whose base comprises cut faces 34. A screw 35 selectively interacts with each of the cut faces so as to securely the position the head in the desired manner. The screw fits in a tapped portion 36 of the socket 32.

When in use, the device is held such that the element 2 rests on the outer portion of the hand joining the index finger to the thumb while the element 3 rests on the middle finger gripped by the thumb, the knob 9 being controlled by the index finger.

The appropriate tool to be used for the particular task to be performed is affixed to the head 18, the head being positioned as desired, by unscrewing the screw 35 and then tightening it after rotating the head to the suitable position. The head is thus held at the angle required to enable the tool to extend in the most suitable direction.

The ratio between the gears or pinions 11, 12, 13 and 15 is selected so as to ensure that the tool will itself be rotated through four rotations of 360 degrees for each rotation of 360 degrees performed by the knob 9.

In view of the above, it is seen that the device of the invention is particularly advantageous for performing operations in conjunction with dental canals and that it can be fitted for such tools as drills, nerve extractors, drill pins, dental cement insertion tools, and even a screwdriver used to tighten or loosen securing screws of pivot teeth.

By virtue of its shape, the instrument is gripped between the thumb and middle finger and rests on the fleshy portion of the hand which extends between the thumb and the index finger. The index finger is free to operate the knob 9 very efficiently without significant effect on the instrument as a whole in terms of its movement. The operation being performed can therefore be carried out with extreme precision.

By virtue of the bayonet-type assembly of elements 2 and 3, shaft 27 and its sleeve 39 may easily be withdrawn from the prolongation 41 such that when the auxiliary operation knob 30 is not required, the kinematic connection between the knob 30 and the shaft 16 is decoupled thus resulting in a reduction of effort required to rotate the knob 9.

By virtue of the frustroconical shape of the knob 9, the user's index finger can be placed thereon without difficulty. Furthermore, by virtue its shape, the shaft 16 may easily be accommodated thus reducing the amount of space required and rendering the tool more compact which is a great advantage from the point of view of visibility of the operating area.

When using the device for removing a securing screw of an obstructed pivot tooth, it may be necessary to hold the screwdriver against the screw with both hands in order to secure the device firmly. In such a situation the knob 30 may be operated by another person.

Although the tool holder is adapted to be used in conjunction with a wide variety of tools, it is to be understood that it is the holder itself which forms the essence of the invention irrespective of the tool being used.

Furthermore, although the invention has been described with respect to particular means and elements, it is to be understood that the invention is not limited to what is specifically disclosed and that the invention is to be construed in light of the claims.

What is claimed is:

1. A tool holder for holding a tool, said tool holder having a bent handle and having first and second ends; said holder comprising:
   (a) a head comprising means for receiving said tool, said head being arranged at said first end of said tool holder;
   (b) an operating knob arranged intermediate said first and second ends, said operating knob being operatively associated with said head whereby rotation of said operating knob results in movement of said tool;
   (c) securing means for securing said head to said holder in a fixed angular position relative thereto, and whereby the angular position of said head is adjustable relative to said handle;
   (d) an auxiliary operating knob arranged at the second end of said holder on said handle, said auxiliary operating knob being operatively associated with said head whereby rotation of said auxiliary operating knob results in movement of said tool; and
   (e) a multiplier system for providing the desired magnitude of movement to said tool in response to movement of said operating knob.

2. The tool holder as defined by claim 1 wherein said head is adapted to rotate said tool.

3. The tool holder as defined by claim 2 wherein said multiplier system is adapted to multiply the amount of rotation imparted to said tool in response to rotation of said operating knob.

4. The tool holder as defined by claim 3 wherein said handle is bent substantially mid-way between said first and second ends.

5. The tool holder as defined by claim 4 wherein holder is bent at an angle of between about 130-160 degrees and said operating knob is arranged inside said angle.

6. The tool holder as defined by claim 5 wherein said operating knob is arranged between said bend and said head.

7. The tool holder as defined by claim 1 further comprising a linkage adapted couple said auxiliary operating knob to said head.

8. The tool holder as defined by claim 7 further comprising decoupling means for decoupling said auxiliary operating knob from said head.

9. The tool holder as defined by claim 8 wherein said linkage comprises a shaft adapted to link said auxiliary operating knob to said head.

10. The tool holder as defined by claim 9 wherein said shaft comprises coupling means located at at least one end thereof for coupling with said linkage, said coupling means being adapted to disengage from said linkage when said decoupling means is arranged to decouple said auxiliary operating knob from said head.

11. The tool holder as defined by claim 10 wherein said handle comprises first and second elements forming said handle, said first element comprising a sleeve adapted to encase said shaft and a longitudinal member adapted to operatively connect said auxiliary operating knob to said shaft.

12. The tool holder as defined by claim 11 wherein said decoupling means comprises a bayonnet connection formed between said sleeve and said second element.

13. The tool holder as defined by claim 12 wherein said second element comprises an outer sleeve surrounding said sleeve of said first element, said outer sleeve comprising at least one slug adapted to cooperate with cut-outs on said sleeve of said first element to form said bayonnette connection.

14. The tool holder as defined by claim 10 wherein said decoupling means comprises a bayonnet connection.

15. The tool holder as defined by claim 1 wherein said operating knob is frustroconical and the small base of said operating knob is arranged in a plane which passes through the median axis of said handle.

16. The tool holder as defined by claim 1 wherein said multiplier system comprises a first pinion mounted coaxialy with said operating knob; a second pinion having a smaller diameter than said first pinion; a third pinion mounted coaxiably with said second pinion and having a greater diameter than said second pinion; and a head shaft operatively connected to said head, said head shaft comprising an arrangement of a plurality of teeth arranged in a smaller diameter than said third pinion; and
   whereby said operating knob is adapted to rotate said first pinion, said first pinion is adapted to rotate said second pinion, said second pinion is adapted to rotate said third pinion and said third pinion is adapted to rotate said system of teeth thereby rotating said head shaft.

17. The tool holder as defined by claim 16 wherein said first and second pinions and said third pinion and said system of teeth intermesh.

18. The tool holder as defined by claim 17 wherein said head shaft is adapted to drive said head.

* * * * *

UNITED STATES PATENT AND TRADEMARK OFFICE
CERTIFICATE OF CORRECTION

PATENT NO. : 4,295,829

DATED : October 20, 1981

INVENTOR(S) : Claude MARTINELLI et al.

It is certified that error appears in the above—identified patent and that said Letters Patent is hereby corrected as shown below:

Column 1, line 59, --assume-- should be inserted after "must".

Column 4, line 40, "the" should be deleted after "securely".

Column 6, line 30, "bayonnet" should be changed to --bayonet--;

line 38, "bayonnette" should be changed to --bayonet--; and line 40, "bayonnette" should be changed to --bayonet--.

Signed and Sealed this

Twenty-sixth Day of January 1982

[SEAL]

Attest:

*Attesting Officer*

GERALD J. MOSSINGHOFF

*Commissioner of Patents and Trademarks*